United States Patent [19]

Schenk et al.

[11] Patent Number: 5,858,803
[45] Date of Patent: Jan. 12, 1999

[54] PROCESS AND REAGENT FOR THE DETERMINATION OF A SPECIFICALLY BINDABLE SUBSTANCE

[75] Inventors: Roland Schenk, Weilheim; Dietmar Zdunek, München, both of Germany

[73] Assignee: Boehringer Mannheim GmbH, Germany

[21] Appl. No.: 376,504

[22] Filed: Jul. 5, 1989

[30] Foreign Application Priority Data

Jul. 5, 1988 [DE] Germany .......................... 38 22 750.9

[51] Int. Cl.[6] ..................................... G01N 33/53
[52] U.S. Cl. .................. 436/533; 436/501; 436/536; 436/518; 436/534; 436/539; 435/7.25; 435/7.5; 435/7.92; 435/7.93
[58] Field of Search ................. 435/7, 7.92, 7.93, 435/7.5, 7.25; 436/501, 536, 518, 533, 534, 539

[56] References Cited

U.S. PATENT DOCUMENTS

| 4,506,009 | 3/1985 | Lenhoff et al. ................ 435/7 |
| 4,829,011 | 5/1989 | Gibbons .................... 436/512 |
| 5,108,896 | 4/1992 | Philo et al. ................ 435/7.5 |

FOREIGN PATENT DOCUMENTS

| 0138297 | 4/1987 | European Pat. Off. . |
| 0232816 | 8/1987 | European Pat. Off. . |
| 02389353 | 9/1987 | European Pat. Off. . |
| 0308242 | 3/1989 | European Pat. Off. . |

Primary Examiner—Toni R. Scheiner

[57] ABSTRACT

The present invention provides a process for the determination of a specifically bindable substance by incubation of the sample solution with at least three receptors $R_1$, $R_2$ and $R_3$, of which $R_1$ and $R_2$ are bindable with one another and $R_3$ is specifically bindable with the substance to be determined and measurement of the agglutination which takes place in the case of the reaction, wherein, as receptor $R_1$, there is used a conjugate of a partner of a specifically binding pair P and of a substance S which corresponds to the substance to be determined or is a derivative thereof and has at least one epitope of the substance to be determined, as receptor $R_2$ there is used a receptor which has at least two binding positions for P and as receptor $R_3$ there is used a receptor which has at least two binding positions, of which at least one binds specifically with an epitope of the substance to be determined or of S. The present invention also provides a reagent for carrying out the above process.

21 Claims, 2 Drawing Sheets

PROCESS AND REAGENT FOR THE DETERMINATION OF A SPECIFICALLY BINDABLE SUBSTANCE

The present invention is concerned with a process for the determination of a specifically bindable substance by incubation of the sample solution with at least three receptors $R_1$, $R_2$ and $R_3$, of which $R_1$ and $R_2$ are bindable with one another and $R_3$ is specifically bindable with the substance to be determined and measurement of the agglutination taking place in the case of the reaction, as well as a reagent suitable therefor.

Many substances are present in body fluids and tissues which are bindable with a specific binding partner and serve as parameter for particular diseases or the state of health of a human body. To these belong, inter alia, haptens, for example hormones, proteins, such as tumour markers, protein hormones and viral proteins, as well as antibodies. For the monitoring of a medicinal treatment, the determination of pharmaceuticals in the blood is also frequently necessary. Since these substances often only occur in very small amounts, immunoassays are frequently used for their detection. For this purpose, there are many variants. The various immunological processes of determination can be divided into homogeneous and heterogeneous processes. In the case of heterogeneous processes, a solid phase reactant always participates in order to separate the bound portion of labelled components from the non-bound ones. In the case of this type of process, the labelling can be determined very well but it is a disadvantage of these processes that the heterogenous reaction takes a long time.

In the case of the homogeneous process variants, no separation of bound labelling from non-bound labelling takes place so that a differentiation of bound and non-bound label must takes place according to other methods.

There are various possibilities for this purpose. Thus, for example,. conjugated enzymes can be used as label which only achieve their enzyme activity when they are bound to the hapten or antigen to be determined or are activated by the substance to be determined. A further possibility involves using a fluorescing substance as label, the fluorescence of which, by binding to the substance to be determined, is either changed into another wavelength range or the polarization of which is altered.

The disadvantages of these known processes include the fact that the sample frequently contains components disturbing the test which makes necessary a pre-treatment of the sample for the removal of these substances. Furthermore, laborious optimization for each parameter is necessary. For example, the enzymes must be modified depending upon the parameter being measured.

U.S. Pat. No. 4,604,365 teaches a process in which the solution containing the hapten to be determined is brought into contact with hapten-coated latex particles or hapten-coated albumin. By the addition of antibodies bindable with the hapten, an agglutination reaction takes place. The hapten in the sample competes with the hapten-coated latex-particles or hapten-coated albumin for binding sites of the antibody. The smaller the agglutination rate, the more hapten is contained in the sample. The disadvantage of this process is the fact that, for each substance to be determined, special particles must be made available and each parameter must be individually A further process for the detection of proteins which depends upon the evaluation of an agglutination reaction is known from published Federal Republic of Germany Patent Specification No. 27 49 956. Antibodies against the substance to be determined are bound directly to the particles capable of agglutination. However, the reactivity of the antibodies is impaired by this binding. Furthermore, such a determination process is subject to disturbances e.g., rheumatism factors.

It is a disadvantage of all known competitive homogeneous agglutination immunoassays that the raw materials must be optimized very laboriously and parameter-specifically. In the case of all of these tests, there are contrary requirements for an optimum differentiation and optimum sensitivity since, on the one hand, the concentration of the particle- reagent is to be limited in order that the competition reaction with the sample is meaningful and, on the other hand, the particle- reagent is to be highly concentrated and highly labelled in order to achieve a sufficient signal change per unit time. The adjustment of these requirements leads to limited sensitivity and susceptibility to disturbances which can often only be overcome by specific pre-treatment of the sample.

Therefore, it is an object of the present invention to provide a homogeneous determination process which makes possible the detection of substances with high sensitivity and exactitude and which does not suffer from the above-mentioned disadvantages Thus, according to the present invention, there is provided a process for the determination of a specifically bindable substance by incubation of the sample solution with at least three receptors $R_1$, $R_2$ and $R_3$, of which $R_1$ and $R_2$ are bindable with one another and $R_3$ is specifically bindable with the substance to be determined and measurement of the agglutination taking place, wherein, as receptor. $R_1$, there is used a conjugate of a partner of a specifically binding pair P and of a substance S, which corresponds to the substance to be determined or is a derivative thereof and displays an epitope of the substance to be determined, as receptor $R_2$, there is used a receptor which has at least two binding positions for P and as $R_3$, a receptor is used which has at least two binding positions of which at least one binds specifically with an epitope of the substance to be determined or of S.

The process according to the present invention can be used for the determination of practically all substances to be detected in body fluids or tissue extracts capable of specific binding, substances in low concentration being detectable just as well as substances in high concentration. The sensitivity and exactitude of the process is improved in comparison with the previously known processes. The present invention provides the possibility of carrying out the determinations quickly and dependably with simple reagents.

The process is especially suitable for the determination of monovalent, specifically bindable substances. As monovalent, there is meant a substance which has only one binding position for a specifically bindable partner. As examples, there can here be mentioned haptens, such as pharmaceuticals. Substances can also be determined which have several binding positions for specifically bindable partners, for example protein hormones, such as HCG (human chorionic gonadotropin) or TSH (thyroid stimulating hormone), antigens and proteins, tumour markers, such as CEA (carcinoembryonic antigen), viral proteins and antibodies.

By epitope, in the description of the present invention is to be understood a binding position which can enter into a specific bond with another substance. Examples of epitopes include antigenic determinants on antigens and haptens but also specific binding sites on proteins.

BRIEF DESCRIPTION OF THE DRAWINGS

The sample solution is incubated with three receptors $R_1$, $R_2$ and $R_3$. The receptors $R_1$ and $R_2$ are bindable with one another and $R_3$ is specifically bindable with the substance to be determined. Various reaction principles which can be carried out with the process according to the present invention are illustrated in FIGS. 1a–1d of the accompanying drawing.

A preferred process variant is the form of carrying out indicated by FIG. 1a. To a sample solution is thereby added receptor $R_1$, is added which is a conjugate of a partner of one pair P specifically binding with member of another member of a binding pair and of the substance S, as well as $R_3$ which is a receptor specifically bindable with the substance to be determined. S, as used herein, is a substance which is identical to the specifically bindable substance to be determined or is a derivative having at least one epitope of the specifically bindable substance to be determined. In the solution, the part S of $R_1$ and the substance to be determined then compete for the binding to $R_3$. If, for example, $R_3$ is a bivalent antibody, then the following complexes are formed:

a. a complex of one $R_3$ and two $R_1$, where $R_1$ is bound to $R_3$ via the S portion;

b. a complex of $R_3$ and two molecules of the substance being determined, and;

c. a complex of one $R_3$, one $R_1$, and one molecule of the substance being determined.

Simultaneously with the other two receptors or after a definite period of time, there is added thereto receptor $R_2$ which has at least two and preferably a plurality of binding positions for P. It thus results in the binding of the receptor $R_1$ via P to receptor $R_2$. Of the complexes present in the solution, only the complexes which have bound at least one receptor $R_1$ bind to $R_2$ and only those in which two receptors $R_1$ are bound to $R_2$ can produce an agglutination, which brings about a photometrically detectable turbidity or turbidity change. The more of the substance to be determined is present in the solution, the less $R_1$ is bound, the less agglutination occurs, and the smaller is the increase of the turbidity. Thus, the extent of the agglutination is an indirect measure for the substance to be determined. This can be evaluated via a calibration curve.

Figure 1A:
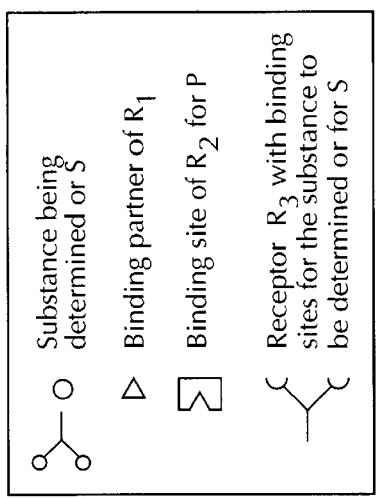
Figure 1A:
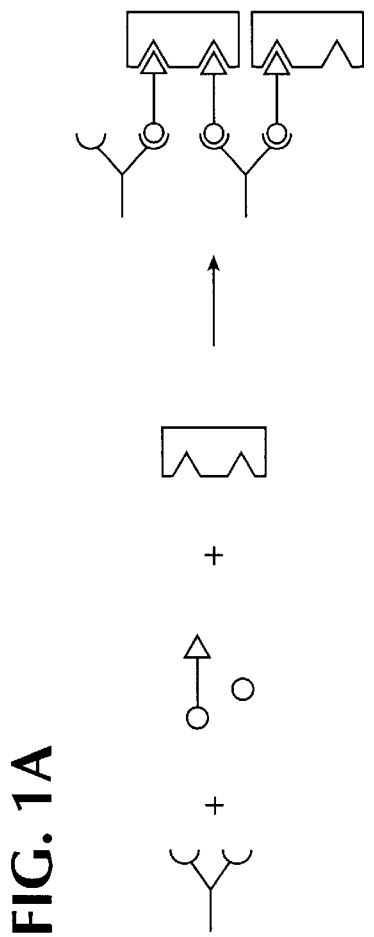
Figure 1B:
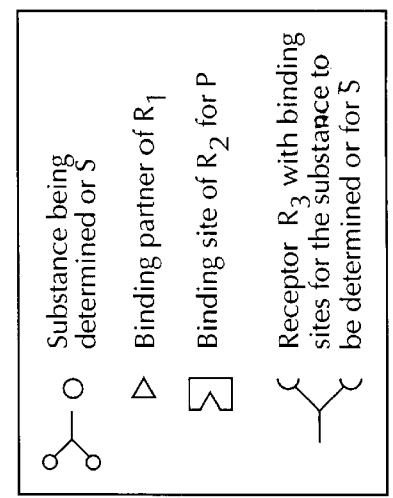
Figure 1B:
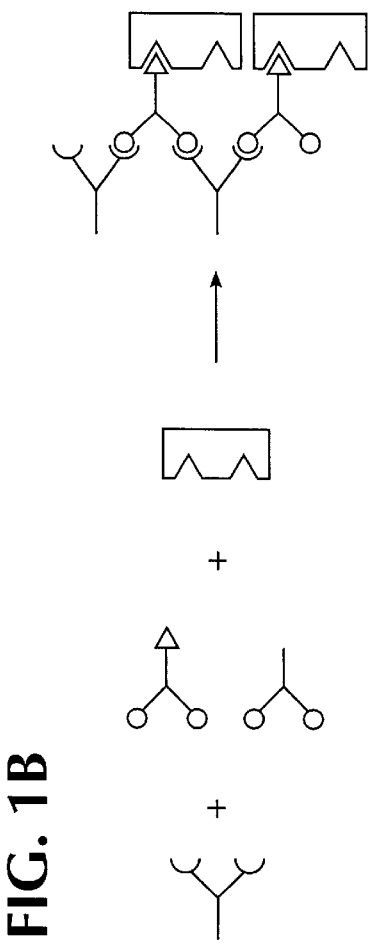

The variant of FIG. 1b serves for the detection of bivalent substances, for example antibodies. The principle is thereby the same as in the case of FIG. 1a). Here, too, only the complexes in which an $R_1$ is bound to the two binding sites of $R_3$ can bring about an agglutination.

Figure 1C:
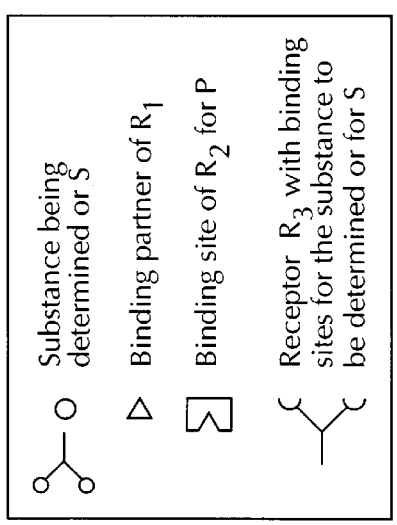
Figure 1C:
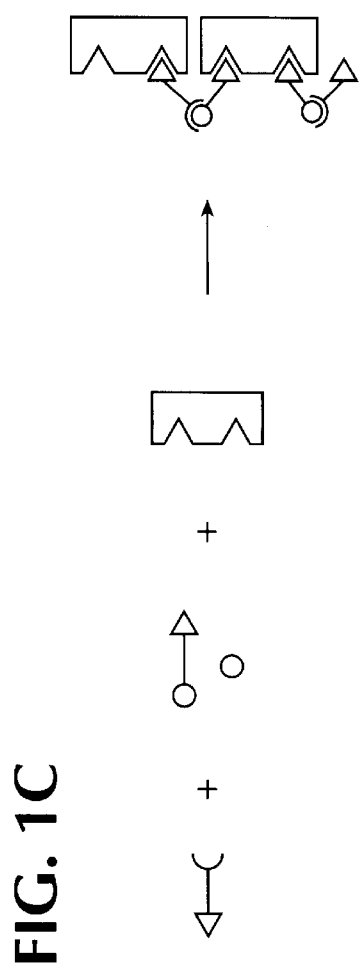

In the case of FIG. 1c, as $R_3$ there is used a conjugate of a receptor specifically bindable with the substance to be determined and a partner of a specifically binding pair. In the case of incubation of the sample solution with $R_1$ and $R_3$, the substance to be determined and $R_1$ again compete for the binding sites of $R_3$. A receptor $R_1$ or a molecule of the substance to be determined can thereby bind to $R_3$. After incubation with $R_2$, the part P of the receptor $R_3$ binds to $R_2$. If, on the other binding position of $R_3$, there is bound the substance to be determined, then cross-linking via $R_2$ is not possible. If, however, the conjugate $R_1$ is bound to the other binding position of $R_3$, then the receptor $R_1$ provides a second binding position for $R_2$ and cross-linking results. In the case of this embodiment, the less $R_1$ is bound, the more of the substance to determined is present in the solution and, consequently, the agglutination formation is then smaller.

Figure 1D:
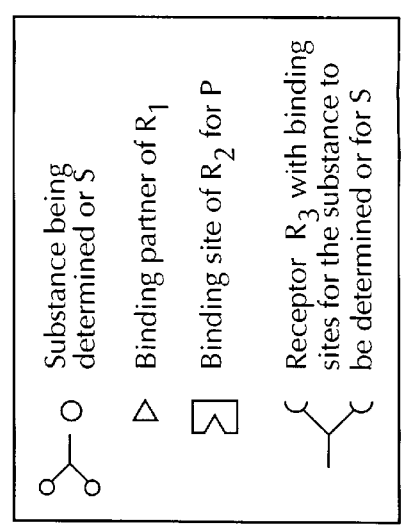
Figure 1D:
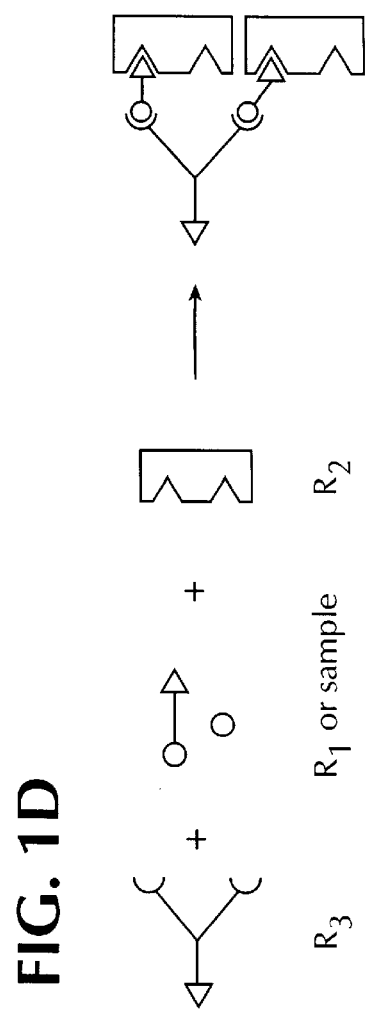

The form of FIG. 1d is a variant of the form of FIG. 1a, whereby, however, as receptor $R_3$ there is used a receptor which, apart from the two binding positions for the substance to determined or S, respectively, has a further binding position in the form of P. In the case of incubation of the sample solution with $R_1$ and $R_3$, the same complexes are again formed as in the case of FIG. 1a). However, in contradistinction to FIG. 1a), not only the receptors $R_3$ to which the two paratopes $R_1$ is bound but also the receptor $R_3$ in which $R_1$ is bound to one paratope and the substance to be determined is bound on the other can bring about an agglutination. Therefore, this embodiment is especially suitable for the detection of substances which are very highly concentrated.

Thus, for the process principle defined according to the present invention, there are many variants for carrying it out. In any case, at least three receptors are necessary. The substance to be determined can be any substance capable of a specific binding and especially, as defined above, a hapten, monovalent, bivalent or polyvalent antigen, antibody or protein.

As first receptor $R_1$, there is used a conjugate which consists of a partner of a specifically binding pair P and a substance S which corresponds to the substance to be determined or a derivative thereof having at least one epitope of the substance to be determined. Pairs specifically bindable with one another are known. Examples of binding pairs (P—$R_2$) which can be used include, for example, biotin-streptavidin or avidin; hapten-antibody; antigen-antibody; concavalin-antibody; sugar-lectin; hapten-binding protein, (for example thyroxine-binding globulin and thyroxine or or oligopeptide-antibody).

Preferred binding pairs include streptavidin-biotin or avidin-biotin. In a particularly preferred embodiment, the receptor $R_1$ contains biotin.

The part S of the receptor $R_1$ preferably corresponds to the unchanged substance to be determined. It can also be a derivative of the substance to be determined or a part of the substance to be determined, for example a protein epitope. The only thing that is important is that the part S is bindable with $R_3$. It is not absolutely necessary that S and the substance to be determined bind to $R_3$ with the same binding force.

The preparation of the conjugates takes place in known manner, for example analogous to the method described in Eur. J. Biochem., 131, 333–338/1980.

The second receptor $R_2$ necessary for the process according to the present invention has at least two binding positions for P and preferably has a plurality of partners of a specifically binding pair complementary to P. The receptor $R_2$ brings about the agglutination of the complex forming in the case of the reaction. Since a plurality of these other partners of the specifically bindable pair are present in the reaction system, a small content of substance bindable with this partner present in the sample solution naturally does not lead to disturbances. The receptor $R_2$ can be a substance which already naturally possesses several binding positions, for example streptavidin or antibodies, Receptor $R_2$ can also be polyvalent and have a plurality of binding positions for P or can be a polymer of the partner of the specifically binding pair complementary to P, for example polystreptavidin. The individual partners are thereby then either bound directly or via bridges with one another. Processes for the preparation of such polymers are well known and do not require a detailed description.

In a further embodiment, the receptor $R_2$ consists of a carrier material to which are bound a plurality of the specifically binding partners complementary to P. As carrier materials, particles which usually have a size of 50 up to 1000 nm can be used. Examples of materials which can be used include polystyrene, finely divided silicon dioxide, erythrocytes, collodial gold-particles or cross-linked albumin. The coating of these particles with the specifically binding partner takes place according to well known methods. Processes of this kind are described, for example, U.S. Pat. No. 4,401,765 and U.S. Pat. No. 4,703,018.

The so coated or polymerized receptors $R_2$ can be used universally for the process according to the present invention and, consequently, are not parameter-specific.

It is important for carrying out the process according to the present invention that the receptor $R_1$ only has one binding site for $R_2$, i.e. that each receptor $R_1$ can only react with one $R_2$. This is an important prerequisite since otherwise $R_2$ could be cross-linked by the receptor $R_1$ alone and thus would bring about an agglutination which is not to be attributed to the substance S to be detected.

The third component essential for the present invention is the receptor $R_3$ which has at least two binding positions of which at least one binds specifically with an epitope of the substance to be determined or of S. This receptor is selected depending upon the substance to be determined. A plurality of receptors is suitable here. For the determination of haptens, proteins, DNA or sugars, it is especially advantageous to use antibodies or other receptors, for example naturally-occurring binding proteins, such as thyroxine-binding globulin, against these substances or fragments thereof. For the determination of DNA, it is also advantageous to use complementary DNA as receptor $R_3$.

When the substance to be detected has only a single binding position for $R_3$, then, in a preferred embodiment, the receptor $R_3$, besides the single binding position for the epitope of the substance to be determined or S, has a binding position different therefrom for a partner of a specifically binding pair in the form of the partner P also used for $R_1$. $R_3$ is then preferably either a conjugate of a partner P of a specifically binding pair and of a substance which has a single binding position which binds specifically with an epitope of the substance to be determined or of S, especially preferably a conjugate of a Fab-fragment specifically binding with an epitope of the substance to be determined or of S and P or a conjugate of a partner P of a specifically binding pair and a receptor which has two binding positions for the epitope of the substance to be determined or S.

The receptor $R_3$ can also have two equal binding positions which bind with an epitope of the substance to be determined or S. Examples of receptors $R_3$ which can be used include monoclonal and polyclonal antibodies, $Fab_2$-fragments and conjugates or Fab fragments and partners of a specifically binding pair. If the receptor $R_3$ is to have more than two binding positions, there can be used conjugates of antibodies, $F(ab)_2$- or $F(ab')_2$-fragments with a partner P. There are here especially preferred biotinylated antibodies and antibody fragments which are specifically bindable with the substance to be determined.

In a further preferred embodiment, receptor $R_3$ is first formed during the determination, for example from an antibody against TBG and two molecules of TBG or an antibody against Fab-fragments and two Fab-fragments.

The process can be carried out in one or more steps. The evaluation takes place by measurement of the extent of the agglutination. Processes for this purpose are known. Thus, for example, there can be used photometric turbidity measurement, the measurement of scattered light by nephelometry, particle counting or photon correlation spectroscopy (PCS).

Since each of the receptors and also the substance to be determined can, in each case, only react specifically with the reaction partner intended for it, it is possible to incubate all receptors and the sample together and to carry out the process in one step. This is especially advantageous in the case of carrying out the process in an automatic analyzer.

For the detection of substances in very low or very high concentration, multi-step process variants are preferred. In the case of the detection of substances present in high concentrations in the sample solution, the following embodiment is preferred. Receptor $R_1$ is thereby first reacted with receptor $R_3$ The part S of the receptor $R_1$, which corresponds to the substance to be determined, and $R_3$ thereby react together. Subsequently, the sample solution is added thereto. The substance to be determined present in this sample solution now displaces the already bound receptor $R_1$ from the binding. Since the proportion of substance to be determined is high in the sample solution, this displacement reaction takes place sufficiently quickly. Subsequently, receptor $R_2$ is added thereto and then the turbidity increase is measured. This manner of carrying out the test is admittedly less sensitive but, nevertheless, is very well suited for highly concentrated samples.

A further preferred embodiment of the process according to the invention is suitable for the detection of substances in very low concentration. As examples, there may be mentioned hormones and pharmaceuticals. Receptor $R_2$ is first pre-mixed with receptor $R_3$ and subsequently the sample is added thereto. The substance to be determined present in the sample thereby reacts with the receptor $R_3$. Agglutination still can not take place since the receptor $R_1$ bringing about the binding of the elements to the receptor $R_2$ is still not present. Subsequently, receptor $R_1$ is added thereto and is bindable with both the receptor $R_3$ and the receptor $R_2$. Here, too, the turbidity increase is measured after a definite period of time. This variant is very sensitive.

For parameters of average concentration, fully competitive assays are also suitable. In this case, receptor $R_1$, receptor $R_3$ and sample solution are incubated simultaneously. The substance to be determined and the part S contained in the conjugate of the receptor $R_1$ compete for the binding on receptor $R_3$. After the addition of receptor $R_2$, the agglutination is then measured.

This variant of the process according to the present invention is also suitable for the detection of haptens which can be coupled with a protein specific for them, the binding protein thereby only having one binding position for the hapten. One example is thyroxine which is specifically bound by thyroxine-binding protein.

The carrying out of all process variants preferably takes place in a buffered solution. Buffer systems for these processes are known. Especially preferred buffers for this purpose are GOOD buffers and phosphate buffers.

According to the present invention, a process is provided which can be carried out simply and quickly and provides a signal which is dependent upon the concentration of the substance to be determined. Since the system responsible for the immunological competition and the signal-forming system are separate, according to the present invention, the sensitivity of detection is increased. With simple reagents, even haptens in low concentration can be quantitatively determined quickly and dependably.

The present invention also provides a reagent for the determination of specifically bindable substances, wherein it contains receptor $R_1$, which is a conjugate of a partner of a specifically binding pair P and of a substance S which corresponds to the substance to be determined or is a derivative thereof and has at least one epitope of the substance to be determined, receptor $R_2$, which has at least two binding positions for P, and receptor $R_3$, which has at least two binding positions of which at least one binds specifically with an epitope of the substance to be determined or of S.

In a preferred embodiment, the reagent according to the present invention can contain the individual receptors $R_1$, $R_2$ and $R_3$ physically separated from one another. In another embodiment, the receptors $R_1$ and $R_3$ can be pre-mixed and the reagent then contains the mixture of $R_1$ and $R_3$ and the receptor $R_2$ physically separated. It is also possible to pre-mix the receptors $R_2$ and $R_3$, the reagent then containing a mixture of $R_2$ and $R_3$ as well as $R_1$ physically separated therefrom.

The reagent according to the present invention can be used for the determination of a plurality of parameters in body fluids and tissue extracts.

In a preferred embodiment, the reagent additionally contains buffer substances and especially preferably it contains phosphate buffer or a GOOD buffer.

The following examples are given for the purpose of illustrating the present invention, reference thereby being made to FIGS. 1a–1d of the accompanying drawing which shows a scheme for the reaction principles of various preferred embodiments of the process according to the present invention.

In all of the illustrated variants, receptor $R_2$ has two binding positions for P. As receptor $R_1$ there is, in each case, used a conjugate of the substance to be determined and a partner P.

FIG. 1a shows a variant which is suitable for the detection of substances which have only one binding position for receptor $R_3$.

As receptor $R_3$, there is here used a receptor which is bivalent with regard to the substance to be determined.

FIG. 1b serves for the determination of bivalent substances, for example antibodies. As receptor $R_3$, there is used a bivalent receptor specifically bindable with the substance to be determined.

FIG. 1c is suitable for the detection of monovalent substances. As receptor $R_3$, there is here used a conjugate of a receptor which has one binding position for the substance to be determined and a partner P.

FIG. 1d is suitable for the detection of monovalent substances. As receptor $R_3$, there is used a conjugate which has two binding positions for the substance to be determined and a partner P.

EXAMPLE 1 a) Preparation of Streptavidin Latex

Streptavidin in a concentration of 2 mg./ml. is incubated in 15 mMol/liter imidazole buffer (pH 7.5) and 100 mMol/liter sodium chloride, together with chloromethylstyrene particles (latex, d=70 nm., corresponding to U.S. Pat. No. 4,703,018) in a concentration of 2% by weight at 55° C. for 24 hours and stirred. After the reaction mixture has been centrifuged for 60 minutes at 20,000 r.p.m., the supernatant is decanted off and the precipitate is taken up in 200 mMol/liter glycine buffer (pH 7.5) containing 0.5% bovine serum albumin, By appropriate dilution, there is prepared a 1% by weight streptavidin latex reagent.

b) Preparation of Hapten-biotin Conjugates

For this purpose, n-butyloxycarbonyltetraiodothyronine and 1-methyl-3-(3'-carboxypropyl)-xanthine (see U.S. Pat. No. 4,156,081) are coupled via pentamethylenediamine with biotin, as described in Eur. J. Biochem. 131, 333–338/1980. There is obtained a $T_4$-biotin conjugate. Theophylline is coupled to biotin in an analogous manner.

EXAMPLE 2

Determination of $T_4$

A reagent consisting of:
900 μl 0.1 mol/liter phosphate buffer (pH 7.5) with 2% polyethylene glycol 40000
20 μl. of sample (aqueous $T_4$ standard)
20 μl. of a 0.1 mg./ml. solution of a polyclonal antibody against $T_4$
20 μl. 1% latex reagent (see Example 1) is incubated for 5 minutes at 37° C. and subsequently
20 μl. of a conjugate of $T_4$ and biotin added thereto concentration of $10^{-6}$ mol/liter.

The kinetics of the turbidity increase is measured and the change of extinction is determined at 405 nm/unit time (5 minutes). The following measurement values are thereby obtained:

TABLE I

| sample (ng./ml. $T_4$) | mE/5 min. |
|---|---|
| 0 | 620 |
| 50 | 500 |
| 100 | 410 |
| 200 | 230 |
| 500 | 60 |

EXAMPLE 3

Determination of Theophylline

A reagent is prepared by mixing
300 μl. 100 mMol/liter Tris buffer (pH 7.5)
7 μl. 1% latex reagent (see Example 1)
7 μl. polyclonal antibody against theophylline (Fab$_2$ "concentration 5 mg./ml.")
and incubated for 5 minutes at 37° C. Subsequently, $5 \times 10^{-6}$ liter of a conjugate of theophylline and biotin are added thereto and the extinction change determined at 450 nm at a time difference of 4.2 minutes. The results are to be seen in Table II.

TABLE II

| sample uM/l theophylline | mE/4.2 min. |
|---|---|
| 0 | 1050 |
| 0.5 | 880 |
| 2.5 | 800 |
| 5 | 550 |
| 12.5 | 320 |
| 25 | 230 |
| 50 | 70 |
| 125 | 40 |

EXAMPLE 4

Comparison with the Prior Art

The process according to the present invention was compared with a process analogous to that of European Patent Specification No. 0,073,611. As coated "carrier", there was used streptavidin which contained 4 $T_4$ molecules per "carrier".

The preparation of this "carrier" took place by mixing together 20 μl. of a conjugate of $T_4$ and biotin (concentration $10^{-4}$ mol/liter) with 20 μl. streptavidin (concentration $2.5 \times 10^{-5}$ mol/liter) and incubating for 30 minutes. After completion of the reaction, this reagent contained $T_4$ which was coupled via biotin to streptavidin.

Carrying Put of the Comparison Experiment

820 μl. 50 mMole phosphate buffer (pH 7.5) and 4% polyethylene glycol 40,000 were mixed together with 40 μl. of the streptavidin reagent prepared as described above and a sample (0 mol/liter $T_4$) added thereto. At the same time, 100 μl. of a solution of 3 mg./liter of antibody against polyclonal antibody against $T_4$ were added thereto and the extinction change per 3 minutes monitored at 340 nm.

Process According to the Present Invention; Variant A

820 μl. 50 mMol/liter of phosphate buffer (pH 7.5) and 4% polyethylene glycol 40,000 were mixed together with 20 μl. of conjugate of $T_4$ and biotin (concentration $10^{-4}$ mol/liter in methanol) and 100 μl. polyclonal antibody against T4 (3 mg./ml.) and incubated for 5 minutes. After the addition of 20 μl. streptavidin (concentration $2.5 \times 10^{-5}$ mol/liter), the change of extinction was monitored per 3 minutes at 340 nm.

Process According to the Present Invention; Variant B

820 μl. 50 mMol/liter phosphate buffer (pH 7.5) and 4% polyethylene glycol 40,000 were mixed together with 20 μl. streptavidin ($2.5 \times 10^{-5}$ mol/liter) and 200 mMol phosphate buffer (pH 7.5) and 100 μl. polyclonal antibody against $T_4$ (3 mg./ml.) and incubated for 5 minutes at 37° C. After the addition of 20 μl. of conjugate of $T_4$ and biotin (concentration $10^{-4}$ mol/liter), the change of extinction was monitored per 3 minutes at 340 nm.

The results of the comparison experiment are:

comparison: 35 mE process according to the present invention, variant A: 646 mE process according to the present invention, variant B: 414 mE.

It is shown that, under analogous conditions, with the process according to the present invention there can be achieved a higher sensitivity in comparison with the process according to the prior art.

We claim:

1. Method for determining a specifically bindable substance in a sample solution comprising incubating said sample with at least three receptors $R_1$, $R_2$ and $R_3$, wherein:
   (a) $R_1$ is a conjugate of a member of a specifically bindable pair P and a substance S which is identical to the specifically bindable substance to be determined or has at least one epitope thereof;
   (b) $R_2$ has at least two binding sites for P and is present in dissolved form in a solution; and
   (c) $R_3$ has at least two binding sites, at least one of which specifically binds with said specifically bindable substance or said at least one epitope thereof, under conditions favoring formation of an agglutination complex between $R_1$, $R_2$, and $R_3$ wherein said specifically bindable substance binds with $R_3$ and prevents formation of said agglutination complex, and measuring formation of said agglutination complex in situ as an inverse measurement of said specifically bindable substance.

2. Method according to claim 1, wherein $R_3$ has a second binding position which specifically binds with an epitope of the specifically bindable substance or with the epitope of S which is identical to an epitope of the specifically bindable substance.

3. Method according to claim 1, wherein $R_3$ has a second binding position which specifically binds to P.

4. Method according to claim 3, wherein said specifically bindable substance has a single epitope which binds with $R_3$ and $R_3$ is a conjugate of a partner P of a specifically binding pair and a substance which has a binding position which specifically binds with said epitope of the specifically bindable substance or with the epitope of S which is identical to said epitope of the specifically bindable substance.

5. Method according to claim 4, wherein $R_3$ is a conjugate of (i) a Fab-fragment which binds with an epitope of the specifically bindable substance or with the epitope of S which is identical to said epitope of the specifically bindable substance, and (ii) P.

6. Method according to claim 3, wherein said specifically bindable substance has a single epitope which binds with $R_3$ and $R_3$ is a conjugate of (i) a partner P of a specifically bindable pair and (ii) a receptor which has two binding positions which specifically bind to the epitope of said specifically bindable substance with the epitope or S which is identical to the epitope of the specifically bindable substance.

7. Method of claim 1, wherein $R_1$ is a conjugate of P and the specifically bindable substance.

8. Method of claim wherein $R_3$ has a plurality of binding partners for P.

9. Method of claim 1, wherein P and $R_2$ are selected from the group of binding pairs consisting of biotin-streptavidin, biotin-avidin, biotin-biotin antibody, antigen-antibody, binding protein-hapten and oligopeptide-antibody.

10. Method of claim 1, wherein $R_2$ is a particulate carrier to which is bound a plurality of binding partners for P.

11. Method according to claim 10, wherein said particulate carrier is polystyrene spheroids, finely divided silicon dioxide, erythrocytes, colloidal gold particles or cross-linked albumin.

12. Method of claim 1, wherein $R_2$ is a polymer of binding partners for P.

13. Method of claim 1, wherein $R_3$ is an antibody specific for the specifically bindable substance or an $F(ab)_2$ fragment which is specific for said specifically bindable substance.

14. Reagent for the determination of a specifically bindable substance comprising receptor $R_1$ which is a conjugate of a partner of a specifically binding pair P and a substance S which is identical to the specifically bindable substance to be determined or is a derivative thereof having at least one epitope of the specifically bindable substance, receptor $R_2$ which is present in dissolved form in a solution and has at least two binding positions for P, and receptor $R_3$ which has at least two binding positions, at least one of which specifically binds with an epitope of the specifically bindable substance or with the epitope of S which is identical to an epitope of the specifically bindable substance.

15. Receptor according to claim 14, wherein $R_1$ is a conjugate of the substance to be determined and of a first partner of a specific binding pair, $R_2$ is an agglutinatable receptor which has a plurality of second partners for the first partner of the specific binding pair and $R_3$ is a receptor for the substance to be determined, wherein $R_1$, $R_2$ and $R_3$ are physically separated from one another.

16. Reagent according to claim 14, wherein the receptor $R_1$, $R_2$ and $R_3$ are physically separated from one another.

17. Reagent according to claim 14, wherein receptor $R_1$ and $R_3$ are mixed and receptor $R_2$ is physically separated therefrom.

18. Reagent according to claim 14, wherein receptors $R_2$ and $R_3$ are mixed and receptor $R_1$ is physically separated therefrom.

19. Reagent according to claim 14, wherein $R_3$ is a conjugate of (i) a partner P of a specifically binding pair and (ii) a substance which has a binding position which binds with an epitope of the specifically bindable substance or with the epitope of S which is identical to an epitope of the specifically bindable substance.

20. Reagent according to claim 19, wherein $R_3$ is a conjugate of (i) an Fab fragment which specifically binds with an epitope of the specifically bindable substance or with the epitope of S which is identical to an epitope of the specifically bindable substance and (ii) P.

21. Reagent according to claim 14, wherein $R_3$ is a conjugate of (i) a partner P of a specifically binding pair and (ii) a receptor which has two binding positions for an epitope of the specifically bindable substance or for the epitope of S which is identical to an epitope of the specifically bindable substance.

* * * * *